United States Patent
Rogacki

(10) Patent No.: US 6,651,654 B2
(45) Date of Patent: Nov. 25, 2003

(54) X-SALIZER AN EXERCISER FOR THE LUNGS

(75) Inventor: Zenon Anthony Rogacki, North Hollywood, CA (US)

(73) Assignee: Zenon A. Rogacki, North Hollywood, CA (US)

(*) Notice: Subject to any disclaimer, the term of this patent is extended or adjusted under 35 U.S.C. 154(b) by 0 days.

(21) Appl. No.: 10/147,404

(22) Filed: May 17, 2002

(65) Prior Publication Data

US 2002/0162560 A1 Nov. 7, 2002

Related U.S. Application Data

(63) Continuation-in-part of application No. 09/274,287, filed on Mar. 22, 1999, and a continuation-in-part of application No. 09/361,326, filed on Jul. 27, 1999.

(51) Int. Cl.[7] .............................................. A61M 16/00
(52) U.S. Cl. ............................ 128/203.12; 128/200.24; 482/13
(58) Field of Search ........................ 128/203.12, 200.14, 128/205.23, 202.22, 200.24, 202.16, 203.25; 604/58; 600/533, 538, 539, 540, 543; 482/13

(56) References Cited

U.S. PATENT DOCUMENTS 5,881,720 A * 3/1999 Vinogradov et al. ... 128/203.15

* cited by examiner

Primary Examiner—Weilun Lo
Assistant Examiner—Mital Patel
(74) Attorney, Agent, or Firm—Gary Bodkins

(57) ABSTRACT

A mode of providing halotherapy to the lower respiratory tract that includes the step of operating a plastic apparatus and inhaling. The plastic apparatus contains sodium chloride (common table salt) User operates the plastic apparatus to release a dosage of salt-filtered air for inhalation when the apparatus is aimed into the user's mouth by way of corrugated plastic tubing and a plastic breathing regulator located next to a plastic mouthpiece. The user then inhales the dosage of salt-filtered air to target the lower respiratory tract (lungs). This dosage of salt-filtered air supplies a concentration adequate to produce potent halotherapy and with continual use, on a daily basis, eliminates dyspnea due to chronic respiratory ailments.

20 Claims, 7 Drawing Sheets

X-SALIZER AN EXERCISER FOR THE LUNGS

CROSS-REFERENCES TO RELATED APPLICATIONS

Figure 1:
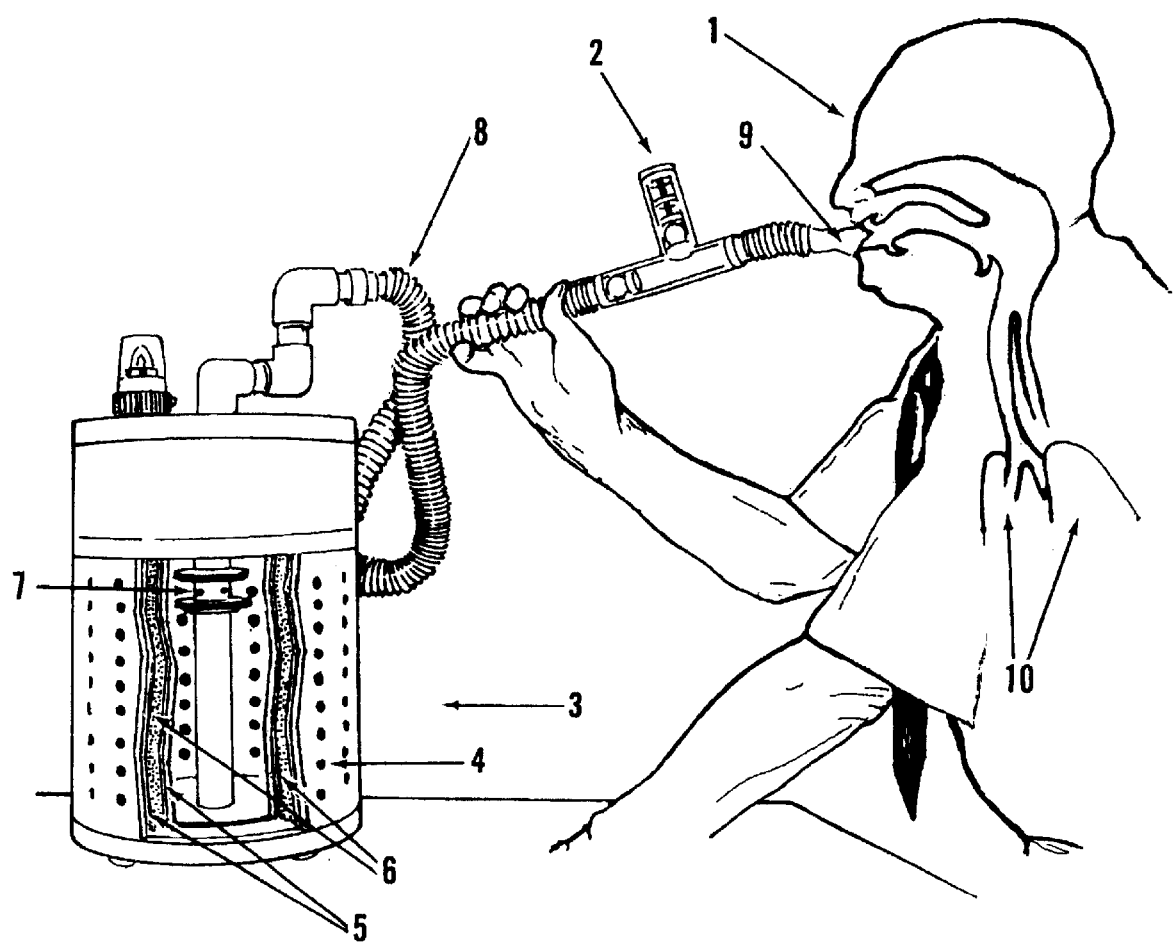

This is a continuation in part of application Ser. Nos. 09/274,287 and 09/361,326 filed Mar. 22, 1999 and Jul. 27, 1999.

BACKGROUND OF THE INVENTION

1. Technical Field

The present invention enumerates to a technique of inhaling salt air (halotherapy) to a person's lower respiratory tract to provide symptomatic treatment for major ailments to a person's lungs such as bronchial and allergic asthma. More expressly, the present invention is designed to provide a method of exercising and strengthening the lungs of a person with major respiratory ailments.

2. Background Art

The usage of inhaling salt air (halotherapy) has been practiced for centuries in eastern Europe in such places as Wieliczka Kapahia, the oldest operating salt mine in Europe. The mine has been in operation for over 800 years and has more than 120 miles of passageways and chambers on nine levels to a depth of more than 1,000 feet. It is used as a sanatorium for people who have bronchial and allergic asthma. Patients live on the surface and are lowered into the mine each day for six hours where they breathe soothing salt air. Wieliczka is eight miles southeast of Krakow, Poland.

In recent times halotherapy has been noted as a powerful drug-free treatment for patients with chronic respiratory ailments. When a salt mine or cave is not available special rooms are created to simulate the atmosphere of the interior of the salt mines. Nevertheless, monetary restraints limit most patients from availing themselves of the healing salt air of the mines or created rooms. This creates a need for a portable apparatus that provides halotherapy treatment to respiratory patients wherever they might be.

It is the main objective of this present invention to supply a method of inhaling salt air for daily treatment and exercise of a patient's lower respiratory tract from a portable inexpensive apparatus.

SUMMARY OF THE INVENTION

The present invention is an apparatus designed specifically to exercise and strengthen the lungs of people with respiratory ailments. It works simply by taking air from the room and allowing it to enter the present invention through two perforated cylinders, one inside the other, that are lined with paper filters. Common table salt is then fully packed the entire space between the two paper filters. The salt-filtered air then enters an inner chamber containing a central pipe with three inhalation holes that are bordered on both sides by two magnets, with like poles repelling each other, that are attached creating a negative magnetic field. After the salted-air passes through the inhalation holes air travels up the central pipe passing through a flotation ball (marble) which is a safeguard designed to prevent exhaling air back into the central pipe and inner chamber. Once the salted-air passes the flotation ball it continues traveling through flexible corrugated plastic tubing to a plastic breathing regulator. The regulator consists of two perfectly suitable plastic cylinders that are assembled at right angles with each other. Primarily it controls, regulates, the air intake of the user. More precisely the exhaled air of the user. This is accomplished by creating resistance in the upright cylinder. Screwing a center bolt in the upright cylinder creates the resistance. Turning one-way, or the other, the regulator creates more or less resistance. The exhaled air of the user is trapped in the regulator and released through the upright cylinder and back into the room where the present invention is placed. This ability to create resistance as the user is exercising and strengthening their lower respiratory tract (lungs) with beneficial salted-air provides a more potent means of halotherapy and as time progresses the user breathes more freely and with greater ease.

BRIEF DESCRIPTION OF THE DRAWING(S)

The present invention is full enlighten by the following specifications in connection with the accompanying drawings wherein:

FIG. 1. A profiled view of the present invention being used by a patient or user.

Figure 2:
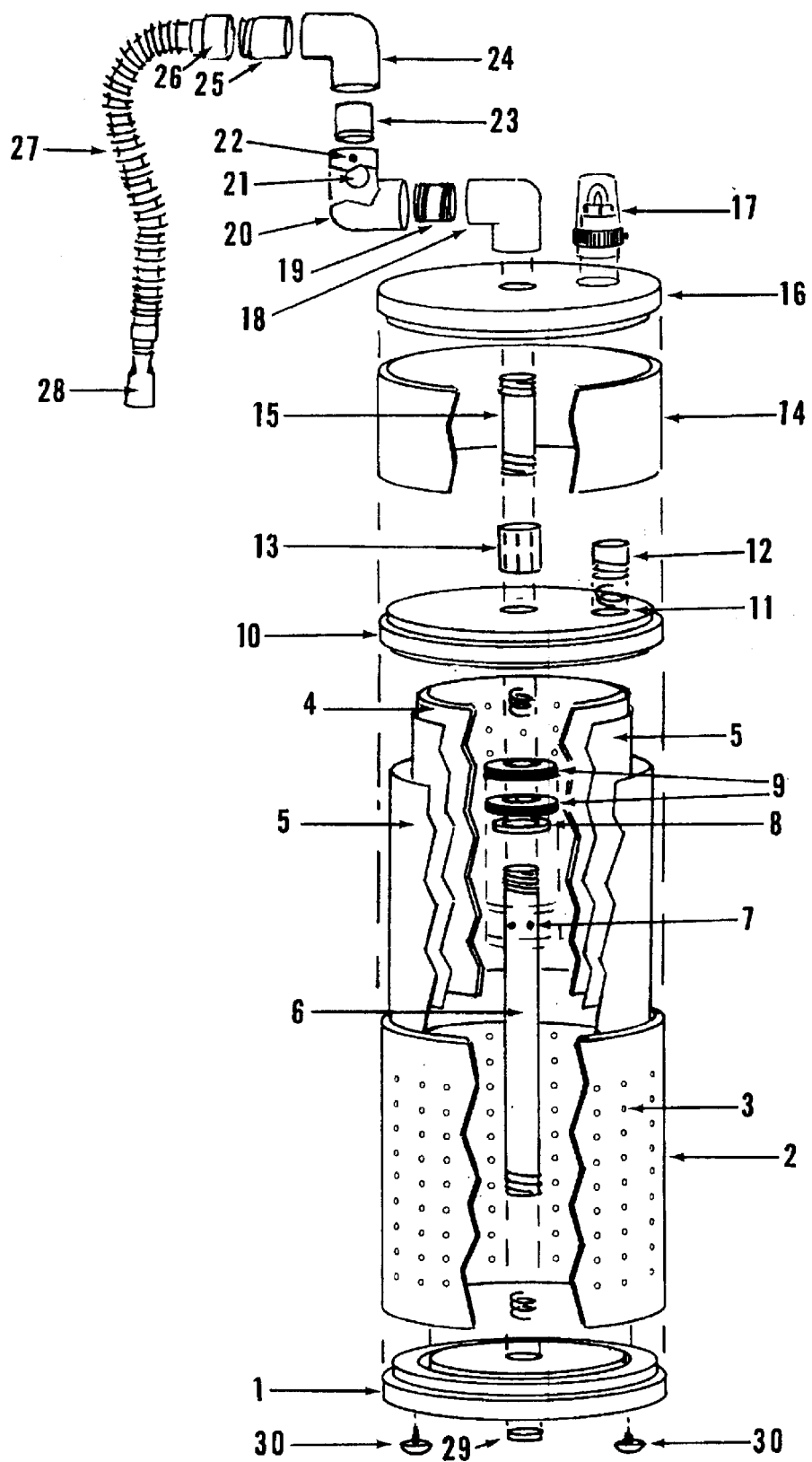

FIG. 2. An exploded view of the present invention illustrating all the assembled parts.

Figure 3:
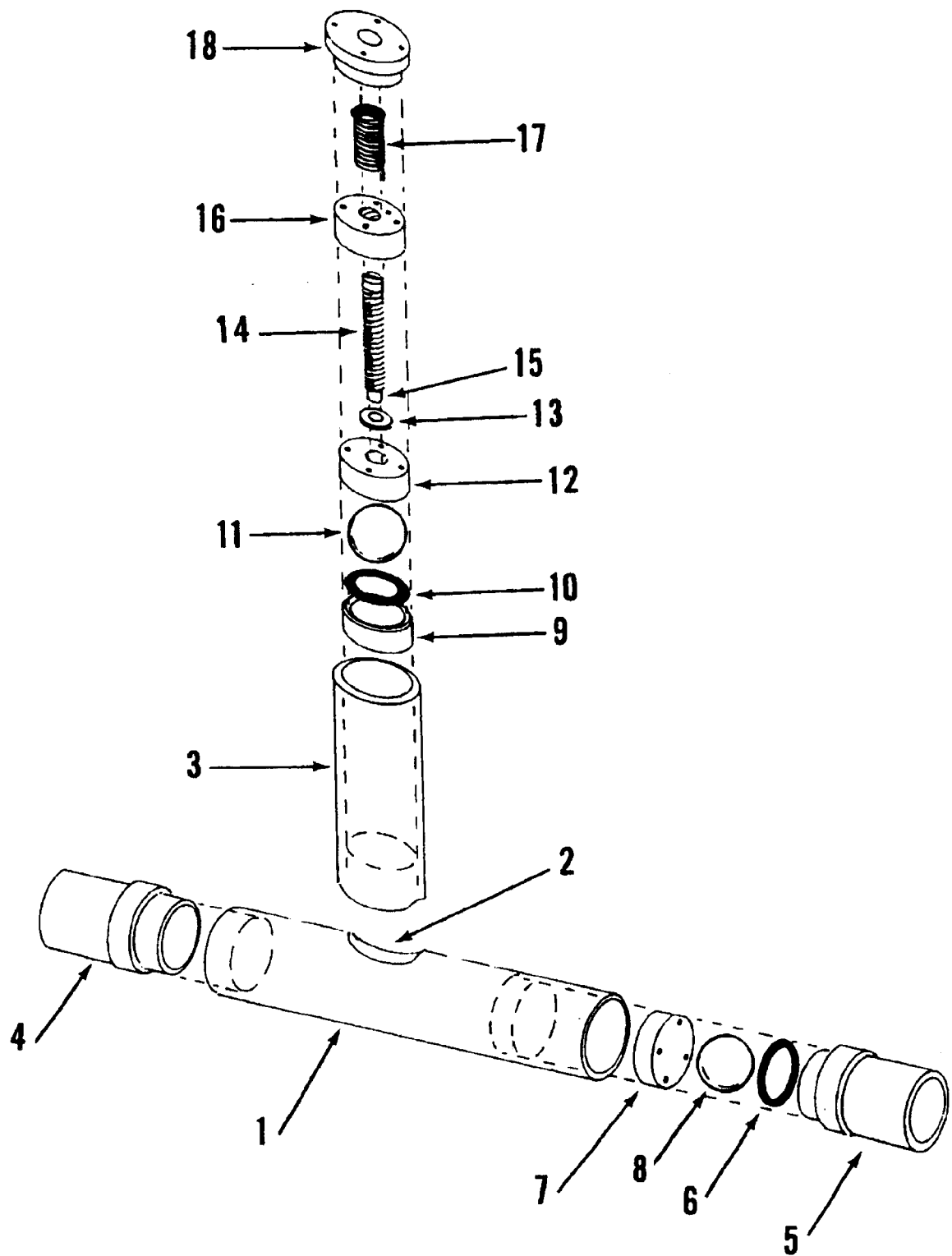

FIG. 3. An exploded view of the breathing regulator of present invention illustrating all the assembled parts FIG. 4. A partial view showing one of the primary functions of the present invention.

Figure 5:
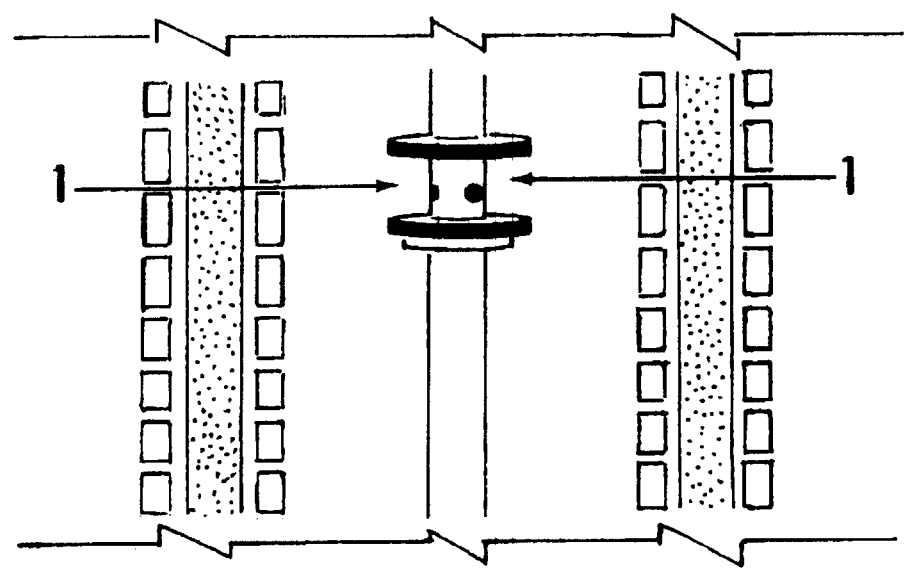

FIG. 5 A partial view showing another one of the primary functions of the present invention.

Figure 6:
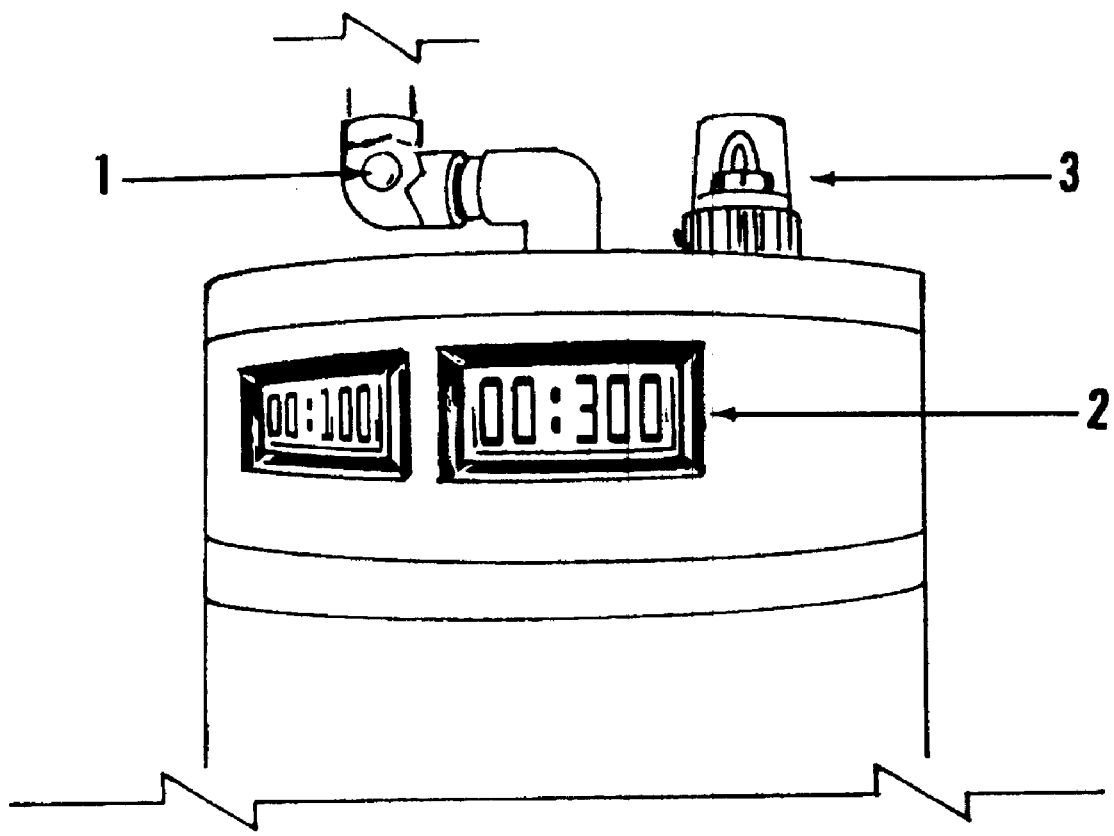

FIG. 6. A partial view of the primary functions of the present invention.

Figure 7:

FIG. 7. A partial view showing one of the primary functions of the breathing regulator of present invention.

Figure 8:

FIG. 8. A partial view showing another one of the primary functions of the breathing regulator of present invention.

Figure 9:
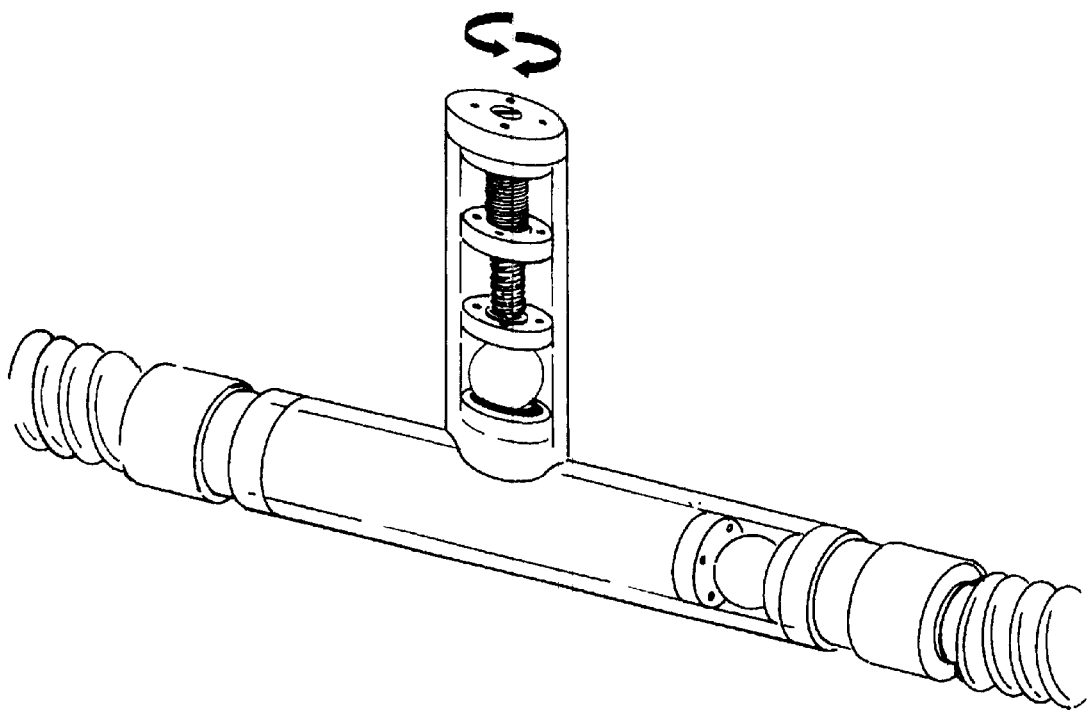

FIG. 9. A partial view of the primary functions of the breathing regulator of present invention.

DETAILED DESCRIPTION OF THE INVENTION

Turning attention to the drawings, more expressly to FIG. 1. there is shown a preferred method of delivering halotherapy of the present invention. Specifically indicated is a halotherapy patient or user 1 utilizing the present invention with a breathing regulator 2 exercising the lower respiratory tract (lungs) of 1 by taking air from the room 3 where the present invention is placed. This allows the air from the room to enter the "X-Salizer" through perforated cylinders 4 that are lined with paper filters 5. The entire space between the paper filters 5 is filled with common table salt 6. This salt-filtered air then travels through a central perfectly suitable plastic pipe 7 drilled with three inhalation holes. As the salt-filtered air enters the central pipe through the inhalation holes it travels up to a length of perfectly suitable flexible corrugated plastic tubing 8 and continues on to a perfectly suitable plastic mouthpiece 9 that is located at the end of the tubing. This mouthpiece is placed in the user's mouth 1 to allow the salt-filtered air to be inhaled into the lower respiratory tract 10 of the user 1.

Now more particularly the present invention is highlighted in FIG. 2. where there is shown an exploded view of all the assembled parts of the present invention which is specifically descripted as an eight inch (diameter) perfectly round grooved plate 1 of perfectly suitable plastic (Plexiglas) that is three-quarters of an inch thick that has been drilled with a half inch hole in the exact center of the plate.

This perfectly suitable round plastic plate is grooved to accommodate first an eight inch, in diameter, perfectly suitable plastic perforated cylinder 2 that is one-eighth of an inch thick and cut to exactly eight inches in length. This plastic cylinder is perforated with one-eighth of an inch drilled holes 3 that are approximately seven-eights of an inch apart both vertically and horizontally around the entire circumference of the eight inch plastic cylinder, except for an inch at the top and the bottom of the cylinder. At this point 2 is inserted into 1.

Next a six-inch in diameter, perfectly suitable plastic perforated cylinder 4 that is one-eighth of an inch thick and cut exactly to a length of eight inches has also been perforated exactly as stated in 3 for 2. This plastic cylinder 4 is now inserted into the inner groove of 1. Next paper filters 5 are inserted covering the entire inside wall of 2 and also covering the entire outside wall of 4. Then a perfectly suitable half of an inch, in diameter, plastic pipe 6 that is exactly ten inches in length and threaded on both ends for screwed assembly is drilled with three inhalation holes that are exactly three-sixteenths of an inch 7 on the upper end of 6. The plastic pipe 6 is screwed into the center-drilled hole of 1 that has also been threaded for screwed assembly. A washer of perfectly suitable metal 8 is inserted just below the inhalation holes on 6. Next two magnets 9 are inserted just below, and above, the inhalation holes on 7. The magnets have like poles repelling each other creating a negative field. Then another perfectly suitable round plastic plate 10 that has been grooved on both sides and drilled with a half of an inch hole in the exact center so it can be inserted into 2, 4, and 6. A half of an inch hole 11 is also drilled through 10 that will allow common table salt to be packed into the entire area between 5. Then a half of an inch threaded perfectly suitable plastic plug 12 is screwed into 11 that has also been threaded for screwed assembly. Next a perfectly suitable plastic coupling 13 that is half of an inch, in diameter, and threaded on both ends is screwed into 6. A perfectly suitable round cylinder 14 that is eight inches, in diameter, and cut to an exact length of two and three-quarters of an inch is inserted into the upper groove of 10. This part 14 creates an upper compartment for gauges. Specifically a digital timer; inhalation meter; and a flash counter 17. Next a perfectly suitable half of an inch plastic pipe 15 that has been cut to exactly three and one half inches in length and threaded at both ends. Part 15 is screwed into 13. Another perfectly suitable round plastic plate 16 that is three-quarters of an inch thick and exactly eight inches, in diameter, that has been grooved on the bottom side. Part 16 also has a half of an inch drilled hole in the exact center is insert into 14. Next a perfectly suitable half of an inch plastic elbow 18 that is threaded at both ends is screwed into 15. Then a perfectly suitable half of an inch plastic pipe 19 that is exactly two and one half of an inch in length that has been threaded on both ends is screwed into 18. Then a perfectly suitable half of an inch plastic elbow 20 that has been threaded on one end is screwed into 19. A perfectly suitable plastic flotation ball (marble) 21 that is five-eights of an inch, in diameter, is placed in the upper section of 20. Part 21 the flotation ball (marble) 21 vibrates as the user is inhaling on this present invention. This vibration activates the inhalation meter located in part 14. The inhalation meter is also connected to the flash counter which is also activated with the vibrations of the flotation ball. The inhalation meter is calibrated to adjust to the exact number of inhalations the user wishes to use in the time they have set on the digital timer also located in part 14. All of this will enable the user of this present invention to adjust the speed of inhalations (example: per hour) making this present invention applicable to all age groups. We highlight particularly the flash counter that indicates to the user when to exhale as it flashes. This creates the proper use of halotherapy for this present invention. In part 14 the digital timer, inhalation meter, and flash counter is activated by one nine-volt battery. Next a three sixteenths of an inch-drilled hole 22 is placed just below the top of 20 large enough to hold a setscrew. Then a perfectly suitable plastic pipe 23 that is half of an inch, in diameter, and exactly two inches in length is inserted into the top of 20 and locked in place with 22 the setscrew. Next a perfectly suitable plastic elbow 24 that is half of an inch, in diameter, is inserted into 22 and glued into place. Then a perfectly suitable plastic pipe 25 that is exactly half of an inch, in diameter, and exactly two inches in length and has been threaded on one end is inserted into 24 and glued into place. Next a perfectly suitable half of an inch in diameter, plastic-coupling 26 that is threaded at one end is screwed into 25. Then a perfectly suitable flexible corrugated plastic tubing 27, that can be any length, is attached to 26. Finally, a perfectly suitable plastic mouthpiece 28 is inserted into 27. A perfectly suitable plastic plug 29 is glued into the center-drilled led hole on the bottom of part 1. At this point only three rubber-covered screws 30 need to be screwed into the bottom of 1. The present invention is now completely assembled and ready to be filled with common table salt 31 and used.

Now more particularly the present invention is highlighted in FIG. 3. where there is shown an exploded view of all the assembled parts of the present invention which is specifically descripted as a four and three-eights of an inch of perfectly suitable plastic cylinder 1 that is one inch, in diameter, that has been drilled with a hole 2 that is exactly three-quarters of an inch, in diameter, that is placed approximately one and one-quarter of an inch from left end of cylinder. Then take a perfectly suitable plastic cylinder 3 that is exactly one inch, in diameter, and exactly two and five-eights of an inch in length and shaped so it fits tightly over drilled hole 2 of 1. Next cement 3 into 1 over drilled hole 2. Then take a piece of perfectly suitable plastic cylinder 4 that is exactly one and one-quarter of an inch in length and one inch, in diameter, that has specifically sized so it will fit tightly into the left end of 1. Now insert 4 into the left end of 1. Then take a second piece of perfectly suitable plastic cylinder 5 that is one inch, in diameter, and cut exactly and sized as 4. Now take a five-eights of an inch perfectly suitable rubber 0-ring 6 and cement it onto the left end of 5. Next take a perfectly suitable plastic disc 7 that has been cut to one-quarter of an inch in length and five-eights of an inch, in diameter, that has also been drilled with four one-sixteenth of an inch holes that are ninety degrees (right angle) from each other and one-sixteenth of an inch from the outer edge of 7. This circular plastic disc is inserted into the right end of 1 until it reaches a length of one and one-quarter of an inch and cemented into place. Then insert a perfectly suitable plastic flotation marble (ball) 8 that is exactly five-eights of an inch, in diameter, into right end of 1 until it touches 7. Next insert 5 into 1 until it almost touches 8. Then take a perfectly suitable plastic cylinder 9 that is one-quarter of an inch thick and three-quarters of an inch, in diameter, and cement a perfectly suitable rubble 0-ring 10 on one side of 9. Next insert 9, with 10, down into the top of 3 until it touches the top of the drilled hole 2 of 1. Then insert a perfectly suitable plastic flotation marble 11 (ball) that is exactly five-eights of an inch, in diameter, into 3 till it rests on top of 11. Next take a perfectly suitable plastic disc 12 that is one-quarter of an inch thick and three-quarters of an inch, in diameter, that has been drilled through with four one-sixteenths holes that are ninety degrees (right Angle) from each other and one-sixteenth of an inch from the outer edge of 12. Plastic disc 12 has also been drilled through in the exact center with an one-quarter of an inch hole. Insert 12 into 3 until it rests just above 11. Next insert a perfectly suitable brass washer 13 that is exactly three-sixteenths of an inch, in diameter, into 3 until it rests over center-drilled hole of 12. Then take a perfectly suitable brass bolt 14 that is one and one-half of an inch in length and one-quarter of an inch, in diameter, that has been threaded and the head removed (headless). The bottom end of 14 has been sized down to exactly three sixteenths of an inch, in diameter, and exactly three-sixteenths of an inch in length 15. Insert 14 into center of 3 until it rests through 13 and into the center drilled hole of 12. Just 15 will enter the center-drilled hole of 12. Next take a perfectly suitable plastic disc 16 that is exactly one-quarter of an inch thick and three-quarters of an inch, in diameter, that has been drilled with four, one-sixteenths of an inch, holes that are ninety degrees form each other. Piece 16 has also been drilled with a hole in the exact center that is one-quarter of an inch, in diameter, and threaded for screwed assembly. Screw 16 onto 14 until it is halfway down, approximately three-quarters of an inch on 16. Then take a perfectly suitable stainless steel spring 17 that is approximately three-eights of an inch, in diameter, and approximately one-half of an inch in length. Slip spring 17 over 14 until, it rest on top of 12 and into a special drilled hole for piece 17. Now cement 17 into place in special drilled hole of piece 12. Lastly take a perfectly suitable plastic disc 18 that is three-eights of an inch thick and one inch, in diameter, that has a center drilled hole through that is exactly one-quarter of an inch in diameter. The bottom half of 18 has been sized down to three-quarters of an inch so it will fit into the top of 3 and become a cap. Piece 18 has also been drilled with four, one-sixteenths of an inch, holes that are ninety degrees (right angle) from each other and one-sixteenths of an inch from the outer edge. Now 18 is cemented into 14. Piece 17 is also cemented into bottom-drilled hole of 18 specially placed to hold 17. It is best to assemble parts 14,16,17, and 18 together and cement parts 17 and 18 into place before you insert parts 14 through 18 into 3.

Now the present invention has been completely assembled and ready to be attached to corrugated plastic tubing of "X-Salizer"

Figure 4:
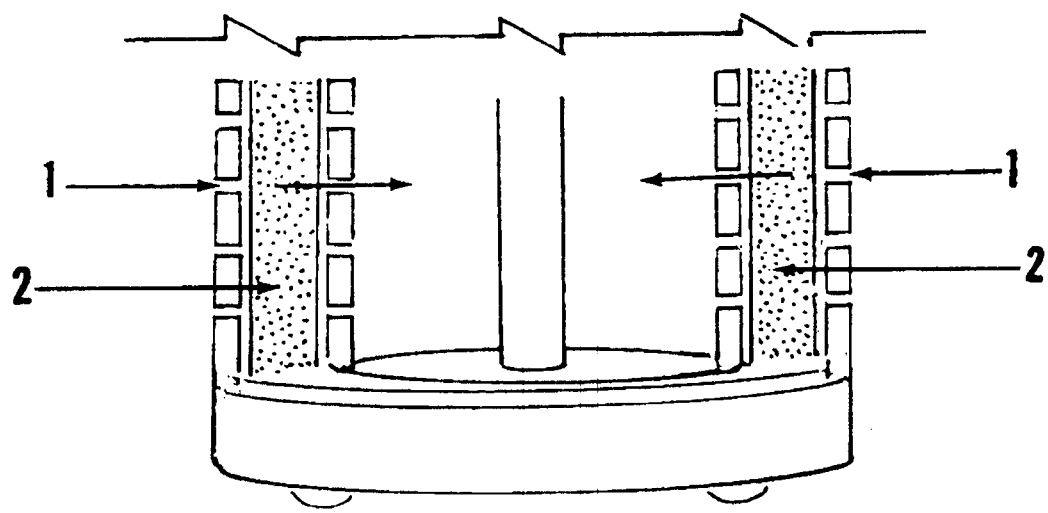

Referring to the present invention in FIG. 4. Particularly the first primary function of the invention: The importance of how the air from the room enters the present invention 1 and immediately becomes salt-filtered air. This is all accomplished by air 1 passing through two paper filters and two inches wide of packed common table salt 2. The salt being fully packed between the paper filters. This creates a very potent concentration of salt-filtered air that enters the inner chamber of the present invention.

Then FIG. 5. highlights the second primary function of the present invention: Salt-filtered air entering the inner chamber. This is created when the salt-filtered air enters a half of an inch, in diameter, perfectly suitable plastic pipe 1 through three inhalation holes that further concentrates the salt-filtered air so the user of the present invention receives the best of halotherapy for exercising and strengthening their lungs (lower respiratory tract)

FIG. 6. turns specifically to the third primary function of this present invention: The operation of the flotation ball (marble) in the upper part of the invention. This involves the process where the salt-filtered air travels through a flotation ball (marble) 1. As the salt-filtered air travels through the flotation ball, the ball vibrates. This vibration activates the inhalation meter 2 that is located inside of part 14. In turn the inhalation meter activates the flash counter 3 also located inside of part 14 and on top of part 16. The inhalation meter is calibrated so it can be adjusted to the exact number of inhalations that are to be used. (example: inhalations per hour). This will enable the user of this present invention to adjust the speed of the inhalations making this present invention applicable to all age groups. As the inhalation meter counts off it activates the flash counter to flash telling the user of the present invention to exhale creating the most effective method of halotherapy. All the foregoing drawings depict a cylindrical plastic apparatus that is constructed entirely of perfectly suitable plastic that will be approximately seventeen inches in height and eight inches in diameter. The plastic apparatus weighs approximately five pounds without the salt and approximately fourteen pounds with the salt added to apparatus.

Referring to the present invention in FIG. 7. Particularly the first primary function of the breathing regulator of invention: Regulation of inhaled salt-filtered air into the user's respiratory system, specially the lower respiratory tract of the user.

Highlighted now in FIG. 8. is the second primary function of the breathing regulator of present invention: Regulation of the exhaled air of the present invention. Particularly how the exhaled air is trapped in the lower cylinder due to the safeguard of the flotation marble (ball) and forced, and released, through the upright cylinder and back into the room.

FIG. 9. turns specifically to the third primary function of this breathing regulator of present invention: Regulation of the exhaled air in the upright cylinder of the breathing regulator. The assembly of the upright cylinder consisting of three plastic discs and a stainless steel spring that are all connected together by a central headless brass bolt that create resistance as the user exhales. This resistance is increased by screwing central headless brass bolt clockwise and decreased by turning central headless brass bolt counter clockwise. As the user breathes, the exhaled air creates resistance in the upper cylinder of the breathing regulator thus strengthening the user's lower respiratory system (lungs) and increases the potency of halotheraphy decreasing dyspnea, due to chronic respiratory ailments, and strengthening the user's lower respiratory tract (lungs) when used on a daily basis.

What I claim my invention is:

1. A process of supplying halotherapy for the purpose of exercising and strengthening the lower respiratory tract (lungs) of a user, said process involving the steps of:

a) operating a cylindrical plastic apparatus that produces, and contains, salt-filtered air, said apparatus releasing a dosage of salt-filtered air for inhalation when aimed into a user's mouth with the use of plastic mouthpiece;

b) administering said dosage of salt-filtered air to the lower respiratory tract (lungs) of user rendering potent halotherapy.

2. The method of claim 1 wherein plastic apparatus includes two paper filtered perforated cylinders.

3. The method of claim 1 wherein dry sodium chloride (common table salt) is contained between two paper filters.

4. The method of claim 1 wherein immediate contact of nine pounds of dry sodium chloride (common table salt) in a two inch wide mass creating a potent concentration of salt-filtered air for inhalation (halotherapy).

5. The method of claim 1 wherein plastic apparatus includes central plastic pipe, with inhalation holes, that further concentrates the potency of the salt-filtered air for halotherapy of lower respiratory tract (lungs).

6. The method of claim 1 wherein plastic apparatus includes two magnets, with like poles repelling each other, creating negative magnetic field where salt-filtered air enters inner plastic channel (inner pipe).

7. The method of claim 1 wherein plastic apparatus includes flexible corrugated tubing of any length.

8. A process of supplying halotherapy to the lower respiratory tract of a user, said process involving the steps of:
   a) operating plastic apparatus that contains operational devices that regulates the pace of the inhalations of salt-filtered air into lower respiratory tract (lungs) of user;
   b) administering said operational devices of the plastic apparatus to establish regulatory stature and continual flow of inhalation into user's lower respiratory tract.

9. The method of claim 8 wherein plastic apparatus includes a flotation ball, a built-in safeguard, designed to prevent exhaling air of user to go back into central pipe and inner chamber.

10. The method of claim 8 wherein salt-filtered air flows through a flotation ball in the upper channel of plastic apparatus which creates vibrations.

11. The method of claim 8 wherein plastic apparatus includes switch that activates inhalation meter that is calibrated; as flotation ball vibrates.

12. The process of claim 8 wherein plastic apparatus includes a flash counter that is activated by the inhalation meter to signal user when to exhale, when they start exercises on plastic apparatus.

13. The method of claim 8 wherein plastic apparatus includes two cylinders assembled at right angles with each other.

14. The method of claim 8 wherein the plastic apparatus involves two rubber o-rings.

15. The method of claim 8 wherein the plastic apparatus contains one, one-quarter of an inch, inner plastic cylinder.

16. The method of claim 8 wherein the plastic apparatus includes four plastic discs of different sizes.

17. The process of claim 8 wherein the plastic apparatus contains one and one-half inch brass headless bolt that regulates resistance by turning bolt clockwise or counter-clockwise.

18. The method of claim 8 wherein plastic apparatus involves a flotation marble in the upper upright cylinder to trap the exhaled air of user and allow it to be released through upper cylinder and back into the room where the present invention is placed.

19. The method of claim 8 wherein plastic apparatus involves perforated discs that regulates the flow of air in breathing regulator of present invention.

20. The method of claim 8 wherein continuous use of plastic apparatus, on a daily basis, will decrease dyspnea.

* * * * *